United States Patent
Ritter

(10) Patent No.: US 7,606,404 B2
(45) Date of Patent: Oct. 20, 2009

(54) METHOD FOR OPTIMIZING PROCEDURES IN RADIOLOGICAL DIAGNOSTICS

(75) Inventor: Herbert Ritter, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 571 days.

(21) Appl. No.: 11/181,087

(22) Filed: Jul. 14, 2005

(65) Prior Publication Data

US 2006/0013457 A1    Jan. 19, 2006

(30) Foreign Application Priority Data

Jul. 14, 2004   (DE) .................... 10 2004 033 991

(51) Int. Cl.
*G06K 9/00* (2006.01)
*G06F 3/00* (2006.01)

(52) U.S. Cl. .................. 382/128; 382/131; 382/132; 715/700

(58) Field of Classification Search ......... 382/128–132, 382/141; 348/86; 715/700
See application file for complete search history.

(56) References Cited

U.S. PATENT DOCUMENTS

| | | | | |
|---|---|---|---|---|
| 6,282,264 | B1 * | 8/2001 | Smith et al. | 378/189 |
| 6,501,849 | B1 * | 12/2002 | Gupta et al. | 382/141 |
| 6,678,703 | B2 * | 1/2004 | Rothschild et al. | 707/201 |
| 6,678,708 | B1 * | 1/2004 | Acharya | 708/308 |
| 2002/0065854 | A1 * | 5/2002 | Pressly | 707/530 |
| 2003/0101075 | A1 * | 5/2003 | Ban et al. | 705/2 |
| 2004/0005033 | A1 * | 1/2004 | Nishihara et al. | 378/169 |

FOREIGN PATENT DOCUMENTS

| | | | |
|---|---|---|---|
| DE | PS 100 58 570 | | 11/2002 |
| EP | 1 262 899 | * | 12/2002 |

OTHER PUBLICATIONS

"Digital Imaging and Communications in Medicine (DICOM)," Supplement 60: Hanging Protocols, DICOM Standards Committee, Working Group 11 Display, Jan. 18, 2005.

* cited by examiner

Primary Examiner—John B Strege
(74) Attorney, Agent, or Firm—Schiff Hardin LLP

(57) ABSTRACT

In a method for optimization of procedures in radiological diagnostics on the basis of digital images (present on a computer of an image workstation) of the same or different modalities in radiological diagnostics, procedure-specific and/or other image processing steps are implemented with using an image processing program on the basis of procedure data that are predetermined and/or newly-entered via a procedure-specifically-configured user interface, until an optimally evaluable result image has been obtained. The procedure steps are implemented by execution of the image processing steps on the basis of the procedure data on the computer. A finding is made and storage of the procedure result in the form of image and finding data is initialized. The procedure result is stored in the form of image and finding data in a memory of the computer. The procedure data that were used and the procedure steps that have occurred are analyzed and are stored as needed.

13 Claims, 4 Drawing Sheets

FIG 2
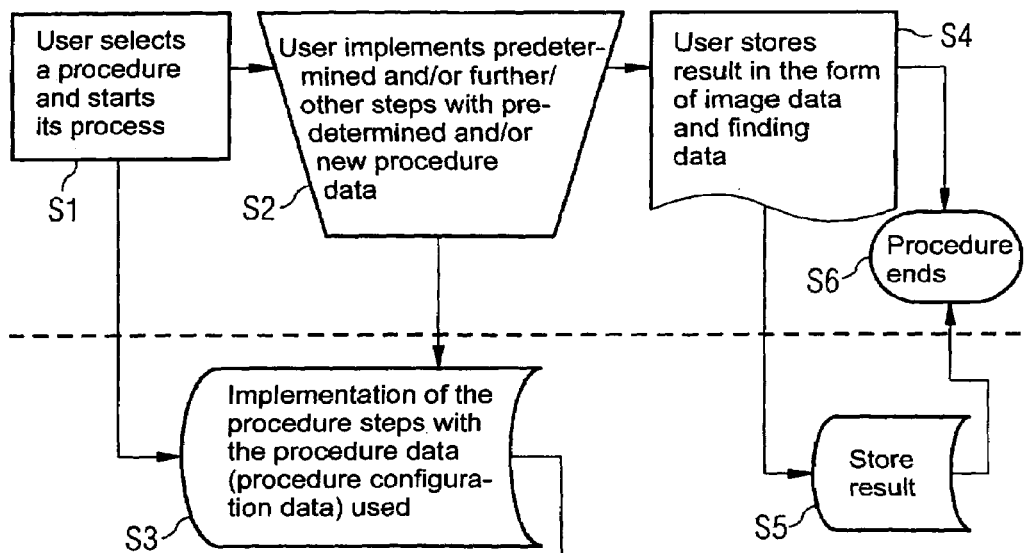
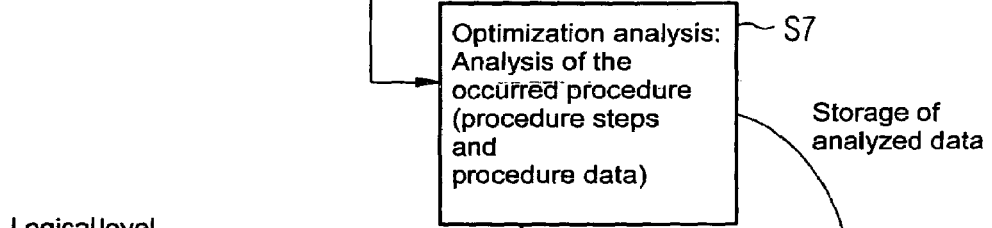
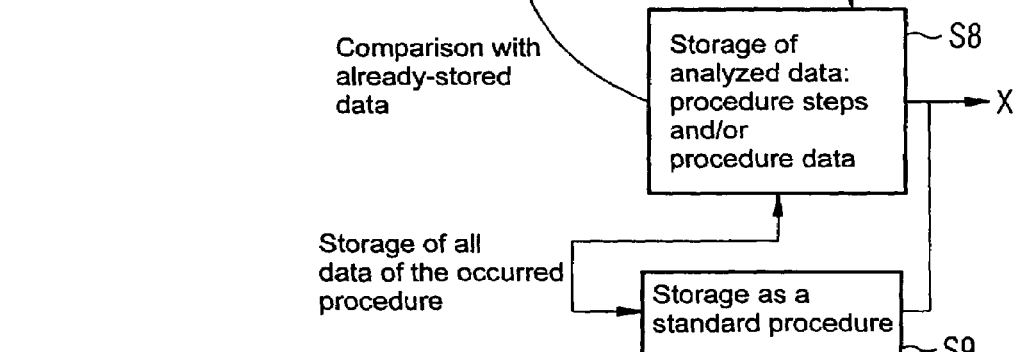

METHOD FOR OPTIMIZING PROCEDURES IN RADIOLOGICAL DIAGNOSTICS

BACKGROUND OF THE INVENTION

1. Field of the Invention

The present invention concerns in general the optimization of procedures in radiological diagnostics. The present invention more particularly concerns an intelligent and thus adaptive data acquisition or image processing in order to achieve an improvement with regard to interface design, training and documentation in radiological image-processing evaluation of medical findings.

2. Description of the Prior Art

Radiological exposures typically exist in digitized form. Examples are tomographic exposures (computed tomography (CT), magnetic resonance tomography (MRT) as well as sonographic exposures (ultrasound (US)) or videos obtained using a laparoscope.

Image workstations of high power and image quality are available to the radiologist for image interpretation and evaluation. The platform of such an image workstation conventionally forms a host computer with high-contrast monitors as a user interface as well as an image memory together with a standardized module library for image-processing programs (tools). The host computer is supported by fast image computers to increase the computation capacity.

Such image workstations are based on complicated hardware and software components that must already be coordinated with one another in the development process. For this purpose, a team of experts from the users and the manufacturer must create and implement a binding, predetermined project phase plan in order to be able to adapt the system to a largest-possible spectrum of task situations.

Such a task defines a workflow that is specified either by the treating physician (house physician, surgeon, etc.) or by the radiologist based on the purpose of the diagnosis. Such a workflow generally begins with the image generation of relevant organs or body parts, with one or more different imaging modalities (CT, MRT, US, laparoscopy, etc.). The images, image series or videos of the body parts and organs acquired by the respective modalities are suitably displayed on the radiological image workstation and respectively subjected to a predetermined or experience-dependent image evaluation process (procedure) until a suitable representation of the corresponding body regions allows a medical finding.

The workflow is ended with the respectively evaluated images being electronically stored with the findings, and possibly with finding data, and being transferred to the treating physician or archived.

A conventional procedure is schematically shown in the flowchart of FIG. 1, starting from a radiological image acquisition that has already occurred, whereby a differentiation is made between the interactive activity of the user by means of keyboard and mouse on the screen, and the algorithmic program process on the computer level that is thereby initiated:

For example, a digital (for example spiral, CT or MRT) overview exposure of the lungs is presented to the user. In order to be able to evaluate the lungs, according to the prior art the user has the possibility of selecting an already-existing procedure and to start its process (step S1). A tool palette 1 thereupon appears on the screen, as shown, for example, in FIG. 4. The tool palette 1 includes a series of buttons, each button symbolizing a specific tool and thus a specific image-processing program. Each tool can be invoked by clicking the corresponding button with the mouse. For example, in FIG. 4 the first button 2 represents an enlargement-shrinking function (zoom). The buttons on the tool palette are dependent on the output image and normally are arranged such that precisely the procedure-specific image processing steps are offered that (for the current output image) lead to a modified image that can be optimally evaluated. The steps are implemented by sequential clicking in the sequence of the arrangement and, if needed, with inputs via the keyboard.

Ultimately, the activity of the user on the screen effects an algorithmic processing by image processing software on the computer level (step S3, which ultimately leads to the evaluable image. The user stores the final image as well as the finding (typically generated in text format) (steps S4, S5) and ends the procedure (step S6).

The user is not forcibly bound to the provided processing steps (Tools) of the or, respectively, a selected procedure; rather, in the event that he deems it to be advantageous, he can invoke further or different tools via a program menu implemented by the manufacturer in order to modify or even generate completely new procedures. For example, in FIG. 4 it is possible for the user to invoke a different tool palette (Tools2) on which further tools are offered.

If a deviation of an image processing series occurs in a procedure, conventionally only the result image is stored with the corresponding finding on the computer level (step S5). The procedural process that ultimately leads to an optimal (because it was evaluable) image, however is not documented according to the prior art.

With presently-existing medical image workstations it is desired by radiologists to optimize (deviating from predetermined workflows and procedures) the image generation, image processing and evaluation in order to increase the patient throughput in radiology, or to make the system operation more efficient and to expand it.

Today's image workstations have no possibility (or a possibility that can be implemented only with a great deal of effort) to introduce optimizations into the system. Without drastic changes to the system software with corresponding changes to the operating instructions, a cost-effective and simple operation oriented to practice is not possible.

Previously an improved operation or a more efficient workflow would have to be recorded via monitoring by test persons (who work on the system under normal conditions) and subsequently integrated into the system in hardware and/or software. The operating manuals would have to be correspondingly amended and the customers specifically trained.

In order to avoid this circumstance, in newer software packages the user interface has been designed to allow it to be changed, dependent on the user, via freely-configurable buttons. Examples for this are generally typical user interfaces such as, for example, Microsoft Office®. This type of configuration is, however, only little known and is therefore mostly used only by advanced program users. It also assumes a relatively high proficiency on the part of the user.

In the framework of medical image workstations it has been shown that the customer expects solutions to the above-described situation from the manufacturer. The present technical implementation is to request support personnel via service centers in order to effect configuration changes (further tools, procedure configuration data, change of tool palettes) on site on the existing system. This ensues, for example, by means of configuration software (see DICOM, "Digital Imaging and Communications in Medicine", Supplement 60, "Hanging Protocols") and is last but not least time-intensive and cost-intensive due to the personnel involvement.

SUMMARY OF THE INVENTION

It is an object of the present invention to design medical image workstations such that a continual optimization of the system ensues without noticeable expenditure of time and service.

This object is achieved according to the invention by a method for optimization of procedures on the basis of digital images (present on a computer of an image workstation) of the same or different modalities in radiological diagnostics including the following steps:

starting a selected procedure, implementing procedure-specific and/or further image processing steps with the aid of one or more image processing programs on the basis of procedure data pre-determined and/or newly-input via a procedure-specifically-configured user interface, until an optimally evaluable result image has been obtained, implementation of the procedure steps by execution of the image processing steps on the basis of the procedure data on the computer, generation of a finding and initialization of the storage of the procedure result in the form of image and finding data, storage of the procedure result in the form of image and finding data in a memory of the computer, ending the procedure, and Subjecting the procedure data that are used and the procedure steps that have occurred to an analysis and are stored, as needed.

The storage can inventively ensue automatically or user-defined on the basis of the result of the analysis, whereby the storage comprises individual procedure steps and/or procedure data.

The analysis can be based on criteria such as the number of the mouse clicks and/or on the number of the image processing programs used and/or on the total duration of the procedure and/or on the quality of the result image subjectively evaluated by the system or user.

According to the invention, in an exceptional case the entire procedure that has occurred is stored as a standard procedure on the basis of an analysis result, or on the basis of a user decision to store all procedure steps that occurred and all procedure data.

The data stored in the storage can inventively be retrieved by user initiation for the following reasons:

configuration data of a stored, selected procedure are read from the storage, and thereupon a corresponding user interface is formed and visualized on the screen, or a standard procedure is read from the storage and is visualized on the screen for demonstration purposes, or data are read from the storage, and from these statistical surveys are made that are visualized on the screen.

The invention also encompasses an apparatus suitable for implementation of the method described above.

The invention also encompasses a computer software product that implements the above-described method running on a computer in a medical image processing system.

DESCRIPTION OF THE DRAWINGS

FIG. 2 is a flowchart of the data acquisition of the inventive method, the data acquisition being based on an analysis of the procedure.

DESCRIPTION OF THE PREFERRED EMBODIMENTS

The invention is based on documenting and analyzing, with suitable data acquisition, procedural workflows in the framework of radiological findings on medical image workstations in order to generate, from the acquired data, inputs for a modified user interface design as well as for a user documentation and training. Additionally, the same data can be used for statistical surveys in order, for example, to evaluate the efficiency on image workstations. For example, it can be detected how long a radiological examination (image generation, image processing and finding) takes on average and how extensive the deviations are. An estimation of the throughput and improvement potential thereby results for radiologists.

The inventive method is explained in more detail in the following using the flowchart according to FIGS. 2 and 3. The nomenclature and organization used roughly corresponds to Nassi-Schneidermann (DIN 66261).

Figure 1:
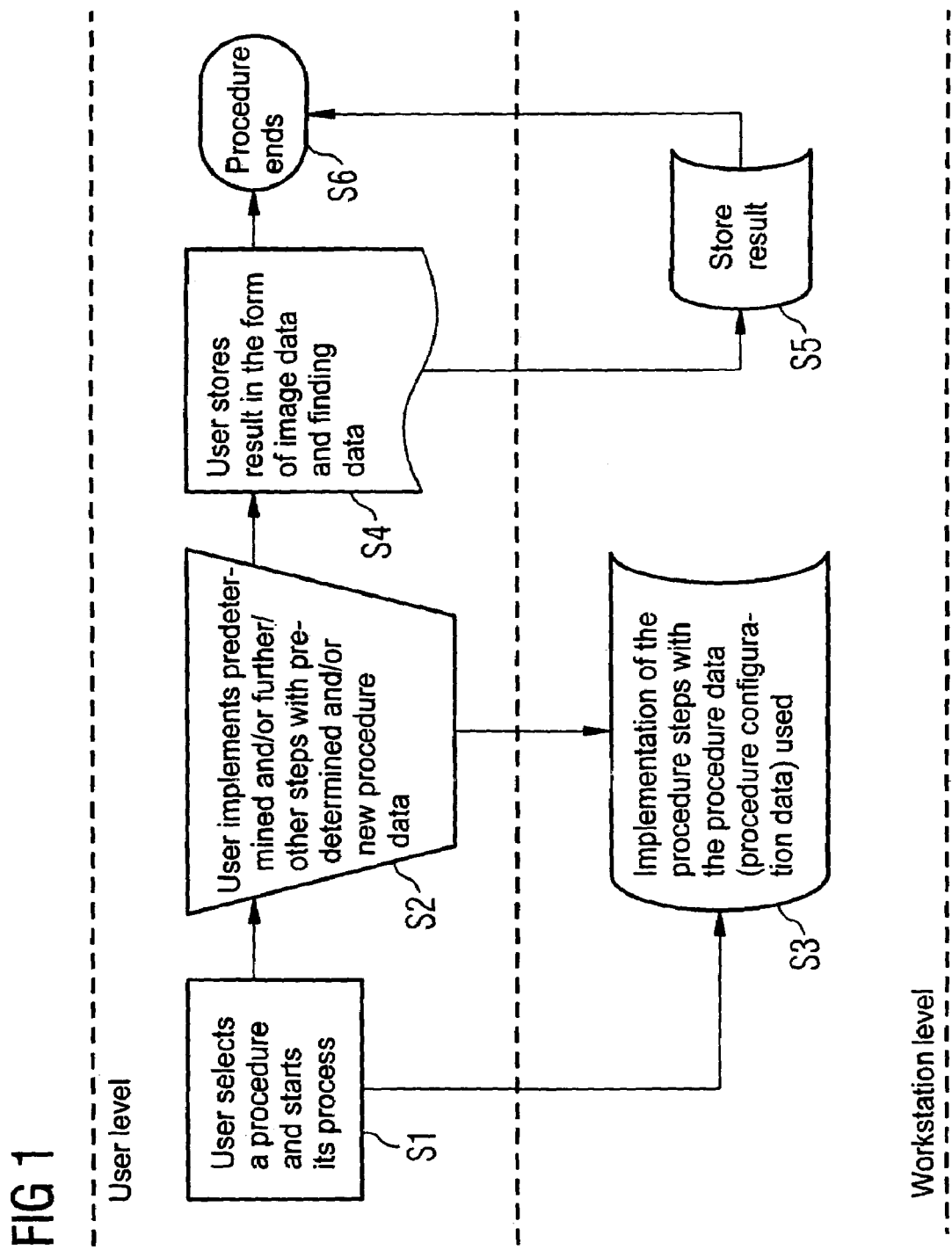
FIG. 1, as explained above, is a flowchart for making a medical finding on a medical image workstation according to the prior art.

The steps S1 through S6 describe the procedural flow for image processing and making a finding at a medical image workstation according to the prior art, already described above using FIG. 1. The user can thereby implement a pre-determined (standard) procedure or deviate from such a pre-determined procedure by using further tools. Given a deviation from stored (standard) procedures, the present invention is applied, by the procedure that occurred in step S3 being analyzed in a step S7, according to optimization criteria. The analysis concerns both the individual procedure steps (the particular tool used) and the procedure data used (procedure configuration data in the form of parameter data sets that the tool accesses, and that can be input or freely selected by the user via user interfaces on the screen).

Criteria for the analysis are, for example, the number of the mouse clicks and/or the number of tools used (number of procedure steps) and/or the total duration of the procedure and/or the quality of the image data or of the finding evaluated by the system or by the user, and/or the invocation frequency of a specific tool etc. A high-quality (and thus optimally evaluable) result image is, for example, an image that was processed such that a diagnosis suspicion can be unambiguously confirmed or unambiguously rejected based on this processed image (under the circumstances in combination with other processed images). It is therefore reasonable to store according to standard procedure procedures that lead to such an optimally evaluable result image as fast as possible based on the analysis, in order to be able to apply this standard procedure or procedures again with similar output images.

If, in the above sense, procedure steps and/or procedure data are deemed to be valuable (for example by validation of a user query) by the user, or by the system based on this analysis, according to step S8 these are stored in a memory of the image workstation insofar as such data are not already stored (a comparison with the already stored data—reverse arrow—optionally ensues in order to prevent storage redundancy). If the analysis yields an advantageous (in multiple respects) evaluation of a procedure that has occurred, according to step S9 this procedure can be adopted as a standard procedure by the user or by the system. In this case all data of this procedure are stored. Such a (now) standard procedure can be used as a new model for a further medical evaluation in a renewal (repeat) of step S1.

If a deviation to a specific tool ensues many times in the framework of a number of procedure executions, a further aspect of the analysis is to detect this and to offer this tool as well through the tool palette when the procedure calls is subsequently involved (called-upon the screen). In such a case, a corresponding button is displayed at a suitable location on the tool palette.

In order to enable this modification or an analysis, the image workstation must be designed so that an architecture composed of a number of levels is present that enables a detection of the relevant data, and is operable using one action control. In addition to the user level and the workstation level, a logical level inventively exists that is in turn coupled to a hardware storage level. "Control action" means that an interaction or information transfer is provided between the individual layers—user level↔workstation level↔logical level ↔hardware storage level.

The procedure selection, the configuration and execution of further steps as well as the initialization of the storage by the user occur on the user level, while the selected procedure with the procedure configuration data is executed on the workstation level and the result is stored in the form of image and finding data. To acquire all data, the steps that the user executes in order to implement the corresponding procedure are registered and configuration data and tools (parameters and functions) are recorded dependent on the task (for example quality control of an overview thorax in radiology). The analysis of the data ensues on the logical level. The result of the analysis is supplied to a data storage in the form of procedure steps and/or procedure data on the hardware storage level.

Figure 3:
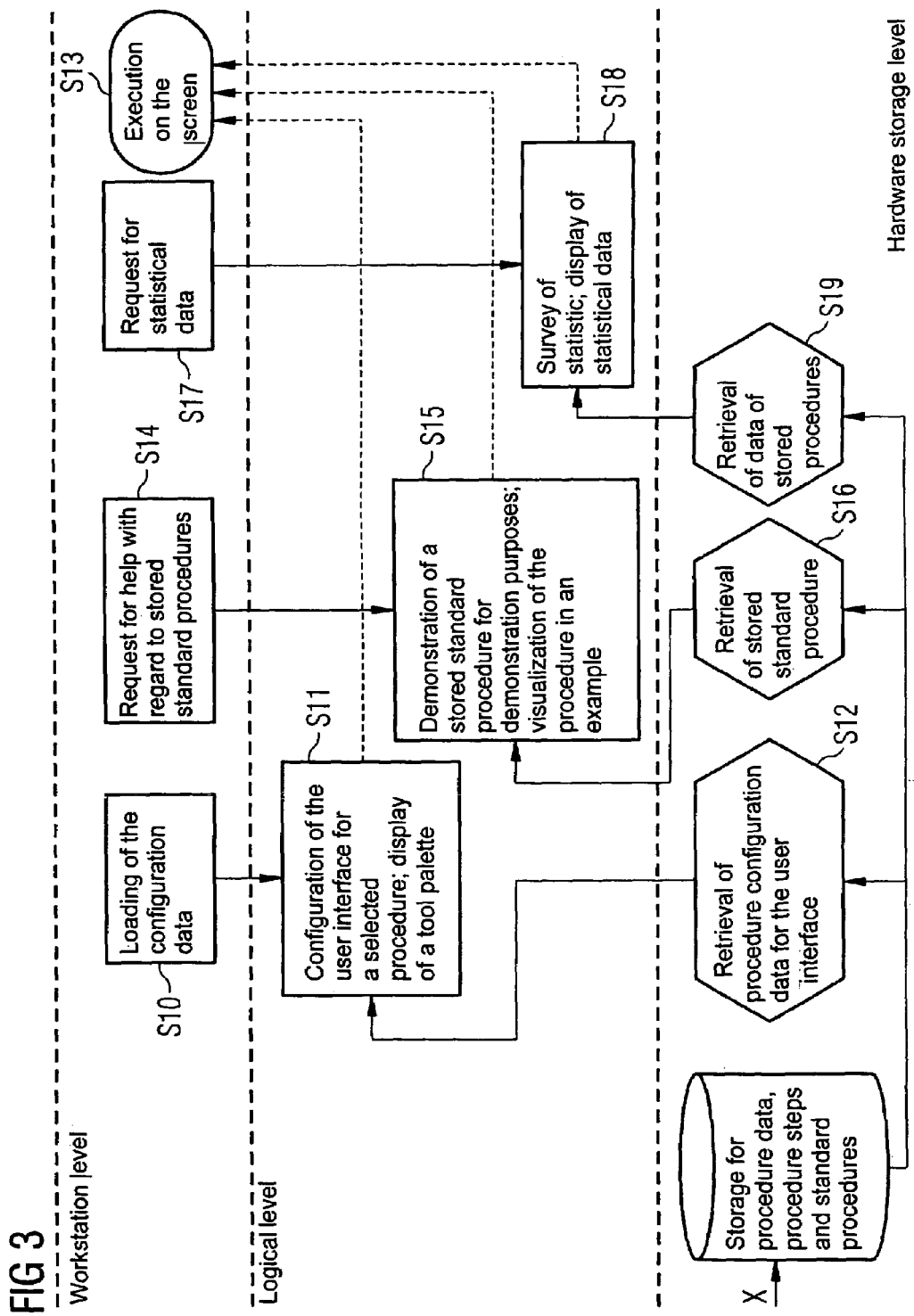
FIG. 3 is a flowchart for the analyzed and acquired data in the framework of the inventive method.
Figure 4:
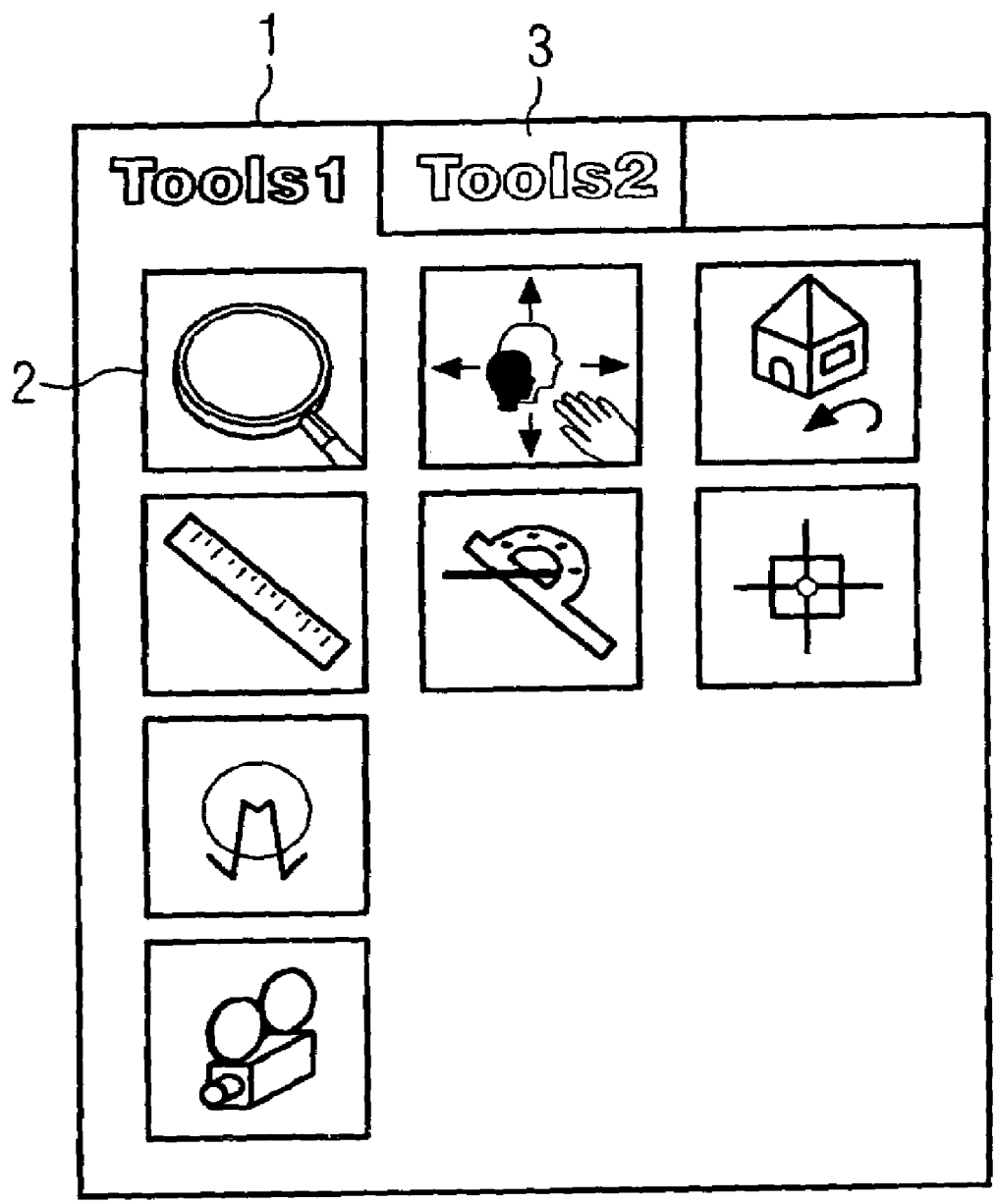
FIG. 4 illustrates a procedure-specific tool palette.

This data storage is shown in the hardware storage level of FIG. 3 and is typically formed of one or more magnetic disks that are written to and read from by means of a write and read head, like a conventional fixed disk storage.

The acquired data (procedure data, procedure steps and standard procedures) are inventively used or invoked again in three respects (FIG. 3):

1. According to step S10, the user initializes loading of configuration data on the user level via the workstation level, whereby according to step S12 procedure configuration data for the user interface are called from the storage located on the hardware level. The user interface is configured for a selected procedure on the logical level on the basis of these data (step S11) and a tool palette corresponding to the procedure is offered to the user on the screen (step S13).

2. The acquired data are used in order to train the user, thus to demonstrate to the user the image preparation of an identical or similar output image on the screen. For this, according to step S14 the user invokes a stored standard procedure via a corresponding help function, which standard procedure is retrieved from the storage according to step S16. In step S15, the process of this procedure is prepared on the logical level for the purpose of the demonstration. The visualization of the process ensues again on the screen according to step S13.

3. In step S17, it is possible for the user to request statistical data in which data of stored procedures (step S19) are read from the storage via the mentioned remote control capability, and in step S18 a statistic selected by the user is surveyed on the logical level. The result is in turn visualized on the screen (S13).

In summary, the invention optimizes procedures via data acquisition during the normal image processing. The acquired data form the basis in order to generate an optimal user interface design, user training and user documentation. The stored information can thus be used in order to view a procedure already stored beforehand in the form of a film playing on a screen. Moreover, using the stored data it can be established which tools are used most, which are then brought into the foreground of the user interface via an appropriate function.

Based on the knowledge of which tools are used most frequently, an increase of the customer usage can be achieved by the functionality of precisely these tools being further developed or improved.

By input data-dependent storage of the tool control elements (for example dependent on the medical case description or diagnosis suspicion), the user interface thus can be adapted to a procedure that is optimal without time-intensive and cost-intensive personnel expenditure.

Finally, with the aid of the stored data operating manuals can be optimized in which the data of various radiological finding methods are collected, compared and analyzed, and the results can be incorporated into the user documents and into the user training as changes to the control panel in the menu navigation.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for optimizing procedures in radiological diagnostics, comprising the steps of:
    displaying at least one acquired digital image that was obtained with at least one medical imaging modality;
    selecting and starting a selected procedure at said computer that is available to evaluate contents of said at least one acquired digital image to make a medical diagnosis from said at least one digital image;
    at said computer, implementing at least image processing steps that are specific to the selected procedure using at least one image processing program that manipulates said at least one acquired digital image using procedure data selected from the group consisting of predetermined data and newly-entered data that are entered via a user interface display that is specifically configured for said selected procedure, until an optimally evaluable resulting image is obtained by processing said at least one acquired digital image;
    in said computer using the optimally evaluable resulting image, generating a medical diagnostic finding via said computer and initializing, via said computer, storage of said optimally evaluable resulting image and data associated with said finding, as a procedure result;
    electronically storing said procedure result in a memory associated with said computer;
    in said computer, analyzing said procedure data and all steps used to obtain said optimally evaluable resulting image to obtain an analysis result; and
    dependent on said analysis result, storing all of said steps used to obtain said optimally evaluable resulting image, as a new standard procedure and making said new standard procedure available at said computer for use as said selected procedure for subsequently processing another acquired digital image.

2. A method as claimed in claim 1 comprising storing said procedure data and said steps used to obtain said optimally evaluable resulting image.

3. A method as claimed in claim 2 comprising automatically storing said procedure data and said steps used to obtain said optimally evaluable resulting image.

4. A method as claimed in claim 2 comprising:
via said computer, allowing user to define a portion of said procedure data and said steps used to obtain said optimally evaluable resulting image; and
storing only said portion defined by said user.

5. A method as claimed in claim 2 comprising individually storing said procedure data and individually storing individual steps from among said steps used to obtain said optimally evaluable resulting image.

6. A method as claimed in claim 1 comprising analyzing said procedure data and said steps used to obtain said optimally evaluable resulting image according to at least one criterion selected from the group consisting of a number of mouse clicks implemented to obtain said optimally evaluable resulting image, a number of image processing programs used to obtain said optimally evaluable resulting image, a total time duration for obtaining said optimally evaluable resulting image, and an image quality of said optimally evaluable resulting image.

7. A method as claimed in claim 1 comprising storing, together with said new standard procedure, configuration data for a new user interface conforming to said new standard procedure, and displaying said new user interface at said computer when said new standard procedure is called via said computer.

8. A method as claimed in claim 1 comprising calling said new standard procedure from memory and displaying said new standard procedure at said computer for a demonstration.

9. A method as claimed in claim 1 comprising storing at least said procedure data used to obtain said optimally evaluable resulting image, and generating a statistical survey from the stored procedure data and displaying said statistical survey at said computer.

10. An apparatus for optimizing procedures in radiological diagnostics, comprising:
a computer supplied with at least one digital image obtained by at least one medical imaging modality, said computer being configured to display a user interface to allow selection of a selected procedure for evaluating contents of said at least one acquired digital image and to start execution of at least image processing steps in said computer that are specific to the selected procedure using at least one image processing program, to manipulate said contents of said at least one acquired digital image using procedure data selected from the group consisting of predetermined data and newly-entered data that are entered via said user interface, said user interface specifically being configured for said selected procedure, until an optimally evaluable resulting image is obtained and displayed at said computer;
said computer being configured to allow the user, using the displayed optimally evaluable resulting image, to generate a medical diagnostic finding and to initialize storage of said optimally evaluable resulting image and data associated with said finding, as a procedure result;
a memory associated with said computer in which said procedure result is stored;
said computer being configured to automatically analyze said procedure data and all steps used to obtain said optimally evaluable resulting image to obtain an analysis result; and
said computer being configured, dependent on said analysis result, to store all of said steps used to obtain optimally evaluable resulting image, as a new standard procedure and to make said new standard procedure available at said computer for use as said selected procedure for subsequently processing another acquired digital image.

11. An apparatus as claimed in claim 10 comprising a memory in which said procedure data and said steps used to obtain said optimally evaluable resulting image are stored.

12. A computer-readable medium encoded with programming instructions for optimizing procedures in radiological diagnostics wherein digital images, obtained with at least one medical imaging modality, are displayed at a computer, said encoded programming instructions when said medium is loaded in said computer, causing said computer to:
allow a user to select and start a selected procedure at said computer that is available for evaluating contents of at least one acquired digital image;
allow a user at said computer, to implement at least image processing steps in the computer that are specific to the selected procedure using at least one image processing program, to manipulate said contents of said at least one acquired digital image using procedure data selected from the group consisting of predetermined data and newly-entered data that are entered via said user interface, that is specifically configured for said selected procedure, until an optimally evaluable resulting image is obtained and displayed at said computer;
allow a user using the displayed optimally evaluable resulting image, to generate a medical diagnostic finding and initialize storage of said optimally evaluable resulting image and data associated with said finding, as a procedure result;
store said procedure result in a memory associated with said computer;
analyze said procedure data and all steps used to obtain said optimally evaluable resulting image to obtain an analysis result; and
dependent on said analysis result, store all of the said steps used to obtain said optimally evaluable resulting image, as a new standard procedure and make said new standard procedure available at said computer for use as said selected procedure for subsequently processing another acquired digital image.

13. A computer-readable medium as claimed in claim 12 wherein said encoded programming instructions further cause said computer to store said procedure data and said steps used to obtain said optimally evaluable resulting image.

* * * * *